United States Patent [19]

Sauers

[11] 4,397,679
[45] Aug. 9, 1983

[54] HERBICIDAL O-SULFAMYLMETHYLBENZENESULFONAMIDES

[75] Inventor: Richard F. Sauers, Hockessin, Del.

[73] Assignee: E. I. Du Pont de Nemours and Company, Wilmington, Del.

[21] Appl. No.: 253,407

[22] Filed: Apr. 27, 1981

Related U.S. Application Data

[63] Continuation-in-part of Ser. No. 168,349, Jul. 11, 1980, abandoned.

[51] Int. Cl.³ ............... A01N 9/22; C07D 239/34; C07D 239/42; C07D 251/46
[52] U.S. Cl. ............................. 71/92; 71/93; 544/194; 544/212; 544/253; 544/278; 544/321; 544/332; 260/545 R
[58] Field of Search ............... 544/332, 321; 71/92

[56] References Cited

FOREIGN PATENT DOCUMENTS 1468747 1/1967 France.
121788 9/1966 Netherlands.

OTHER PUBLICATIONS

Ouf, et al., "J. Drug Research," vol. 6, No. 2, 1974, pp. 123–129.·
Logemann, et al., "Farmaco Ed. Sci.," vol. 12, No. 7, 1975, pp. 586–593.
Wojciechowski, "Acta Pol. Pharm.," vol. 19, No. 2, 1962, pp. 121–125.

*Primary Examiner*—Donald G. Daus
*Assistant Examiner*—James H. Turnipseed

[57] ABSTRACT

The compounds are of the class of N-[(substituted pyrimidin-2-yl)aminocarbonyl]-2-(sulfonylmethyl)benzenesulfonamides, useful as preemergent or postemergent herbicides or plant growth regulators.

22 Claims, No Drawings

HERBICIDAL O-SULFAMYLMETHYLBENZENESULFONAMIDES

RELATED APPLICATION

This application is a continuation-in-part of my copending application U.S. Ser. No. 168,349, filed July 11, 1980 (now abandoned).

BACKGROUND OF THE INVENTION

α,2-Toluenedisulfonamide derivatives are useful as agricultural chemicals and in particular as herbicides.

French Pat. No. 1,468,747 discloses the following para-substituted phenylsulfonamides, useful as antidiabetic agents:

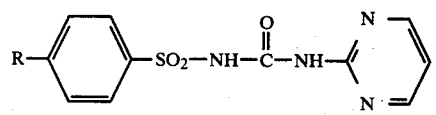

where R=H, halogen, CF$_3$ or alkyl.

Logemann et al., Chem. Ab., 53, 18052 g (1959), disclose a number of sulfonamides, including uracil derivatives and those having the formula:

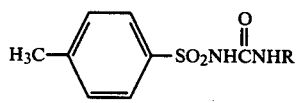

wherein R is butyl, phenyl or

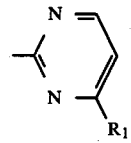

and R$_1$ is hydrogen or methyl. When tested for hypoglycemic effect in rats (oral doses of 25 mg/100 g), the compounds in which R is butyl or phenyl were most potent. The others were of low potency or inactive.

Wojciechowski, J. Acta. Polon. Pharm. 19, P. 121–5 (1962) [Chem. Ab., 59 1633 e] describes the synthesis of N-[(2,6-dimethoxypyrimidin-4yl)aminocarbonyl]-4-methylbenzenesulfonamide:

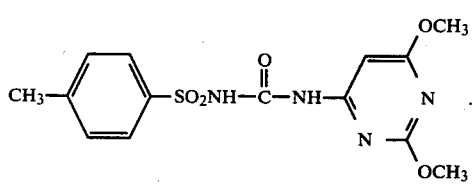

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides:

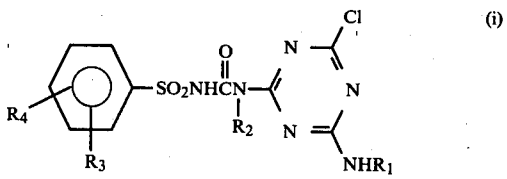

wherein
R$_1$ and R$_2$ may independently be alkyl of 1–4 carbon atoms; and
R$_3$ and R$_4$ may independently be hydrogen, chlorine or alkyl of 1–4 carbon atoms.

Compounds of Formula (ii), and their use as antidiabetic agents, are reported in *J. Drug. Res.* 6, 123 (1974):

wherein R is pyridyl.

The presence of undesired vegetation causes substantial damage to useful crops, especially agricultural products that satisfy man's basic food needs, such as soybeans, wheat and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I and their agriculturally suitable salts, suitable agricultural compositions containing them and their method of use as general herbicides.

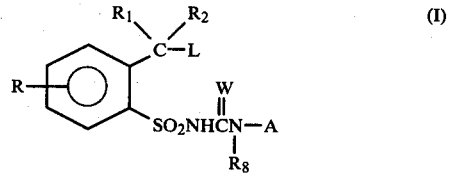

wherein
L is SO$_2$NR$_3$R$_4$;
R is H, F, Cl, Br, NO$_2$, CF$_3$, C$_1$–C$_3$ alkyl or C$_1$–C$_3$ alkoxy;
R$_1$ is H or C$_1$–C$_4$ alkyl;
R$_2$ is H or CH$_3$;
R$_3$ is C$_1$–C$_4$ alkyl or OCH$_3$;
R$_4$ is C$_1$–C$_4$ alkyl;
R$_8$ is H, CH$_3$ or OCH$_3$;
A is

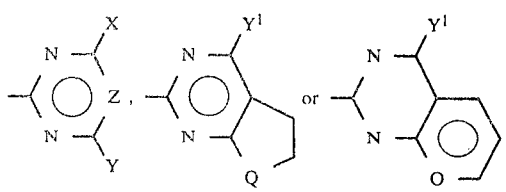

W is O or S;

X is H, Cl, Br, CH$_3$, CH$_2$CH$_3$, C$_1$-C$_3$ alkoxy, CF$_3$, SCH$_3$ or CH$_2$OCH$_3$;

Y is CH$_3$ or OCH$_3$;

Z is N, CH, CCl, CBr, CCN, CCH$_3$, CCH$_2$CH$_3$, CCH$_2$CH$_2$Cl or CCH$_2$CH=CH$_2$;

Y$^1$ is H, CH$_3$, OCH$_3$ or OCH$_2$CH$_3$; and

Q is O or CH$_2$;

and their agriculturally suitable salts; provided that:

(1) when R$_3$ is OCH$_3$, then R$_4$ is CH$_3$;

(2) the total number of carbon atoms of R$_3$ and R$_4$ is five or less; and (3) when W is S, then R$_8$ is H. Preferred in increasing order for their higher activity and/or more favorable ease of synthesis.

(1) Compounds of the generic scope wherein Z is N, CH, CCl, CBr or CCH$_3$, W is O, and R$_8$ is H or CH$_3$;

(2) Compounds of Preferred (1) wherein Z is CH or N, X is CH$_3$ or OCH$_3$, and R$_1$ and R$_2$ are H;

(3) Compounds of Preferred (2) wherein A is

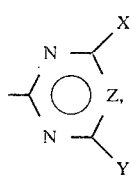

and R and R$_8$ are H;

(4) Compounds of Preferred (3) wherein R$_3$ is C$_1$-C$_3$ alkyl or OCH$_3$, and R$_4$ is CH$_3$; and (5) Compounds of Preferred (4) wherein R$_3$ is OCH$_3$ or CH$_3$.

Specifically Preferred for highest activity and/or most favorable ease of synthesis are:

2-[(Dimethylamino)sulfonylmethyl]-N-[(4,6-dimethylpyrimidin-2-yl)aminocarbonyl]benzenesulfonamide, m.p. 203°–204° C.;

2-[(Dimethylamino)sulfonylmethyl]-N-[(4,6-dimethoxypyrimidin-2-yl)aminocarbonyl]benzenesulfonamide, m.p. 171°–176° C.;

2-[(Dimethylamino)sulfonylmethyl]-N-[(4-methoxy-6-methylpyrimidin-2-yl)aminocarbonyl]benzenesulfonamide, m.p. 181°–183° C.;

2-[(Dimethylamino)sulfonylmethyl]-N-[(4,6-dimethyl-1,3,5-triazin-2-yl)aminocarbonyl]benzenesulfonamide, m.p. 209°–210° C.;

2-[(Dimethylamino)sulfonylmethyl]-N-[(4,6-dimethoxy-1,3,5-triazin-2-yl)aminocarbonyl]benzenesulfonamide, m.p. 200°–203° C.; and 2-[(Dimethylamino)sulfonylmethyl]-N-[(4-methoxy-6-methyl-1,3,5-triazin-2-yl)aminocarbonyl]benzenesulfonamide, m.p. 200°–205° C.

This invention also relates to novel compounds of Formula II which are useful intermediates for the preparation of the herbicidal compounds of Formula I.

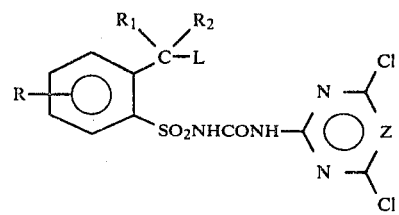

wherein

L, R, R$_1$, and R$_2$ are as previously defined, and

Z is CH or N.

This invention also relates to novel compounds of Formula III which are useful intermediates for the preparation of the compounds of Formula I.

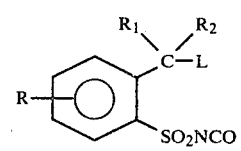

wherein L, R, R$_1$ and R$_2$ are as previously defined.

DETAILED DESCRIPTION

Synthesis

The compounds of Formula I, in which W=O, may be prepared as shown in Equation 1 by the reaction of an appropriately substituted benzenesulfonyl isocyanate with an appropriate aminopyrimidine or aminotriazine.

Equation 1

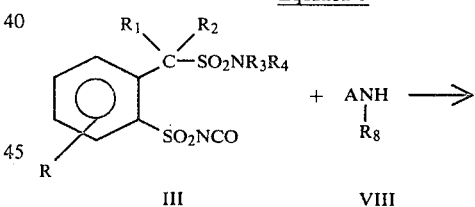

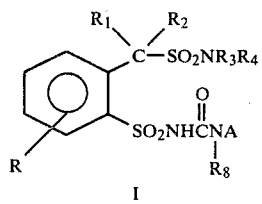

wherein

R is H, F, Cl, Br, NO$_2$, CF$_3$, C$_1$-C$_3$ alkoxy or C$_1$-C$_3$ alkyl;

R$_1$ is H or C$_1$-C$_4$ alkyl;

R$_2$ is H or CH$_3$;

R$_4$ is C$_1$-C$_4$ alkyl;

R$_3$ is CH$_3$O or C$_1$-C$_4$ alkyl; provided that when R$_3$ is CH$_3$O, then R$_4$ is CH$_3$, and provided that the total number of carbon atoms of R$_3$ and R$_4$ is five or less;

A is

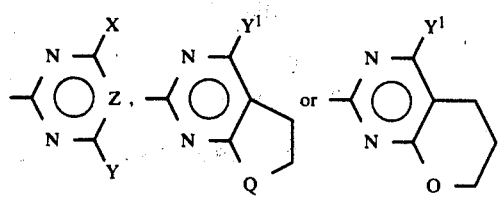

X is H, Cl, Br, CH₃, CH₃CH₂, C₁-C₃ alkoxy, CF₃, CH₃S or CH₃OCH₂;

Y is CH₃, CH₃O or Cl;

Z is N, CH, C-Cl, C-Br, C-CN, C-CH₃, C—CH₂CH₃, C-CH₂CH₂Cl or C—CH₂CH=CH₂;

Y¹ is H, CH₃, CH₃O or OCH₂CH₃; and

Q is O or CH₂.

The reaction of Equation 1 is best carried out in an inert aprotic solvent such as methylene chloride, tetrahydrofuran or acetonitrile at a temperature between 20° and 80°. A catalytic amount of 1,4-diazabicyclo[2,2,-2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, ethylether or methanol and filtration.

The benzenesulfonyl isocyanates of Formula III may be prepared as shown below in Equation 2, by phosgenation of the sulfonamides of Formula IV in the presence of butyl isocyanate. The sulfonyl isocyanates of Formula III may also be prepared, as shown in Equation 3, by phosgenation of the butyl ureas of Formula V.

Equation 2

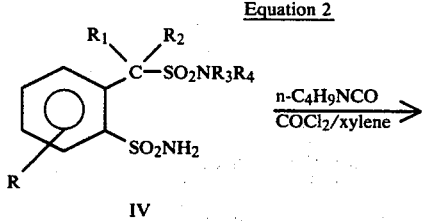

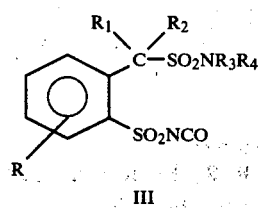

wherein R, R₁, R₂, R₃ and R₄ are as previously described.

The above reaction is carried out by heating a mixture of the appropriate sulfonamide (IV), an alkyl isocyanate such as butyl isocyanate and a catalytic amount of a tertiary amine such as 1,4-diaza[2,2,2]bicyclooctane (DABCO) in xylene, or other inert solvent of boiling point ≧135° to approximately 135°. Phosgene is then added to the mixture over a 1-6 hour period until an excess of phosgene is present as indicated by a drop in the boiling point to less than 130°. The mixture is cooled and filtered to remove a small amount of insoluble by-products. The solvent and the alkyl isocyanate are distilled off in-vacuo leaving a residue of the crude, sulfonyl isocyanate, III, which can be used without further purification.

Equation 3

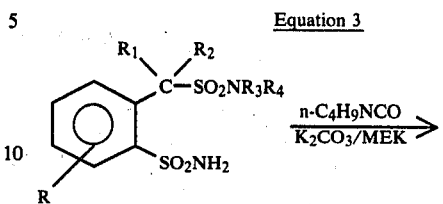

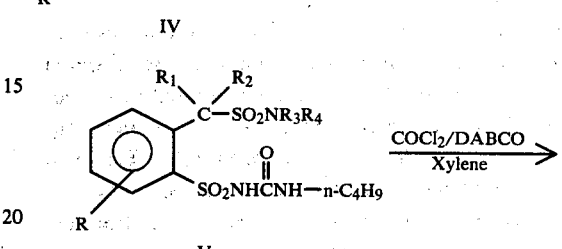

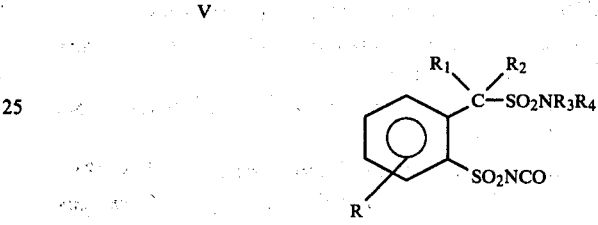

wherein R, R₁, R₂, R₃ and R₄ are as previously described.

The compounds of Formula V are conveniently prepared by stirring a mixture of the sulfonamides, IV, anhydrous potassium carbonate, and n-butyl isocyanate in acetone or methyl ethyl ketone at 25°–80° until all of the isocyanate has reacted. The products are isolated by quenching in dilute mineral acid and recrystallizing the solid product. The compounds V are treated with phosgene and a catalytic amount of DABCO in refluxing xylene or chlorobenzene in a manner analogous to that described in Equation 2.

The sulfonyl isocyanates of Formula III may also be prepared as shown in Equation 4, by the method of Ulrich et al. [J. Org. Chem. 34, 3200 (1969)].

Equation 4

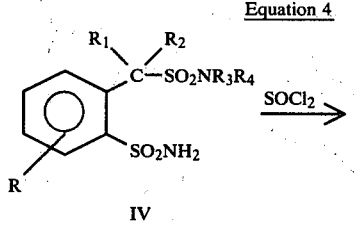

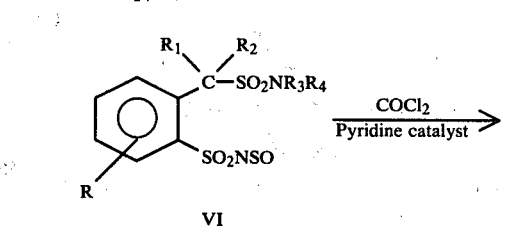

-continued
Equation 4

$$\underset{\text{III}}{\text{[Ar(R)(C(R_1)(R_2)SO_2NR_3R_4)(SO_2NCO)]}}\quad 5$$

The synthesis of heterocyclic amine derivatives such as those depicted by Formula VIII has been reviewed in "The Chemistry of Heterocyclic Compounds", a series published by Interscience Publ., New York and London. Aminopyrimidines are described by D. J. Brown in "The Pyrimidines", Vol. XVI of the above series.

The synthesis of the bicyclic pyrimidines of Formula VIII is described in the following references:

Braker, Sheehan, Spitzmiller and Lott, *J. Am. Chem. Soc.* 69, 3072 (1947).

Mitter and Bhattacharya, *Quart. J. Indian. Chem. Soc.* 4, 152 (1927).

Shrage and Hitchings, *J. Org. Chem.* 16, 1153 (1951).

Caldwell, Kornfeld and Donnell, *J. Am. Chem. Soc.* 63, 2188 (1941).

Fissekis, Myles and Brown, *J. Org. Chem.* 29, 2670 (1964).

All of the above are herein incorporated by reference.

Compounds of Formula I, in which W=O, can also be prepared by the method described in Equation 5.

Equation 5

$$\text{IV} + \text{VII} \longrightarrow \quad (5a)$$

$$\text{II} \longrightarrow \quad (5b)$$

-continued
Equation 5

$$\text{IX} \quad$$

$$\text{IXa} \longrightarrow \quad (5c)$$

$$\text{X}$$

$$\text{IIa} \longrightarrow \quad (5d)$$

$$\text{XI}$$

wherein
R, $R_1$, $R_2$, $R_3$ and $R_4$ are as described previously;
$R_{12}$ is methyl;
$R_{13}$ is $C_1$-$C_3$ alkyl;
$X_2$ is Cl or Br;
$Y_2$ is H, Cl, Br, methyl, ethyl or $CF_3$;
$Y_3$ is Cl or Br;
$Y_4$ is methyl, ethyl or $CF_3$; and
E is $CH_3S$—.

REACTION STEP (5a)

In Reaction Step (5a), an aromatic sulfonamide of Formula IV is contacted with a heterocyclic isocyanate of Formula VII to yield an N-(haloheterocyclicaminocarbonyl) aromatic sulfonamide of Formula II.

The heterocyclic isocyanates used in Reaction (5a) may be prepared according to methods described in Swiss Pat. No. 579,062, U.S. Pat. No. 3,919,228, U.S. Pat. No. 3,732,223 and *Angew Chem. Int. Ed.* 10, 402 (1976), the disclosures of which are herein incorporated by reference.

The aromatic sulfonamide and the heterocyclic isocyanate are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110° C., and the product can generally be recovered by cooling and filtering the reaction mixture. For reasons of efficiency and economy, the preferred solvents are acetonitrile and THF, and the preferred temperature range is about 60° to 85° C.

REACTION STEPS (5b) AND (5c)

In Reaction Steps (5b) and (5c), one or two of the halogen atoms on the heterocyclic ring of the compound of Formula II is displaced by a nucleophilic species. Generally, this may be done by contacting the compound of Formula II either with alkanol, $R_{12}OH$, or with alkoxide, $-OR_{12}$, where $R_{12}$ is as defined above.

Thus, in Reaction Step (5b), a compound of Formula II, substituted with one displaceable group, can be contacted with at least one equivalent of alkanol, $R_{12}OH$. This reaction is sluggish, however, and it is preferred to contact the compound of Formula II with at least two equivalents of alkoxide, $-OR_{12}$. The alkoxide can be provided in a number of ways:

(a) The compound of Formula II can be suspended or dissolved in an alkanol solvent, $R_{12}OH$, in the presence of at least two equivalents of alkoxide, $-OR_{12}$. The alkoxide can be added directly as alkali metal or alkaline earth metal alkoxide or can be generated by the addition to the alkanol solvent of at least two equivalents of a base capable of generating alkoxide from the solvent. Suitable bases include, but are not limited to, the alkali and alkaline earth metals, their hydrides and tert-butoxides. For example, when $R_{12}$ is methyl, the compound of Formula II could be suspended or dissolved in methanol in the presence of two equivalents of sodium methoxide. Alternatively, two equivalents of sodium hydride could be used in place of the sodium methoxide.

(b) The compound of Formula II can be suspended or dissolved in an inert solvent in the presence of at least two equivalents of alkoxide, $-OR_{12}$. Suitable inert solvents include, but are not limited to, acetonitrile, THF and dimethylformamide. The alkoxide may be added directly as alkali metal or alkaline earth metal alkoxide or may be generated from alkanol and a base as described in (a) above. For example, when $R_{12}$ is methyl, the compound of Formula II could be suspended or dissolved in THF in the presence of two equivalents of sodium methoxide. Alternatively, two equivalents each of methanol and sodium hydride could be used instead of sodium methoxide.

For reasons of economy and efficiency, procedure (a) is the more preferred method.

It should be noted that two equivalents of alkoxide are required for Reaction Step (5a) whereas only one equivalent of alkanol is needed for the same process. This difference is due to the reaction which is believed to occur between the alkoxide and the sulfonyl nitrogen of the sulfonamide of Formula VIII. When alkoxide is used, the first equivalent of alkoxide removes a proton from the sulfonyl nitrogen, and it is only the second equivalent which effects displacement of the halogen. As a result, two equivalents of alkoxide are required. The resulting salt must be acidified, e.g., with sulfuric, hydrochloric or acetic acid, to yield a compound of Formula IX. Applicant, of course, does not intend to be bound by the mechanism described above.

In Reaction step (5c) a compound of Formula IXa, substituted with at least one displacement group, is contacted with either one equivalent of alkanol, $R_{13}OH$, or with two equivalents of alkoxide, $-OR_{13}$ where $R_{13}$ is as described above. The compound of Formula IXa is prepared according to Reaction Step (5b) from a compound of Formula IX where $Y_2$ is Cl or Br. When alkoxide, $-OR_{13}$ is used, it may be provided in either of the methods described above in connection with Reaction Step (5c), and the resulting salt can be acidified to yield a compound of Formula X.

When $R_{12}=R_{13}$, Reaction Steps (5b) and (5c) may be combined. Thus, a compound of Formula II may be contacted either with at least two equivalents of alkanol, $R_{13}OH$, or with at least three equivalents of alkoxide, $-OR_{13}$.

When a compound of Formula II contains two displaceable groups, i.e., both $X_2$ and $Y_2$ are Cl or Br, certain reaction conditions will favor displacement of only one of the group. These conditions are the use of low temperatures and, when alkoxide is used, the slow addition of the stoichiometric amount of alkoxide or alkoxide-generating base to the medium containing the compound of Formula II.

When alkoxide is used, both Reaction Steps (5b) and (5c) are preferably run at temperatures within the range of about $-10°$ to 80° C., the range of about 0° to 25° C. being more preferred. Reaction Steps (5b) and (5c) are more sluggish when alkanol is used instead of alkoxide, and more drastic conditions are required for the reaction to go to completion. Thus, higher temperatures, up to and including the boiling point of the alkanol itself, are required.

REACTION STEP (5d)

Reaction Step (5d) involves the displacement of the halogen atom in a compound of Formula IIa by a methylthio nucleophile. The starting material, a compound of Formula IIa, is prepared according to Reaction Step (5a), and $Y_4$ is limited to $C_1$-$C_2$ alkyl and $CF_3$.

For this reaction, the compound of Formula IIa is suspended or dissolved in an inert solvent, such as acetonitrile or THF. At least one equivalent of the nucleophilic species and at least two equivalents of a base are then contacted with the starting material. The first equivalent of base is believed to neutralize the sulfonamido proton. The second equivalent of base generates mercaptide ion from the mercaptan. Suitable bases include sodium hydride, sodium methoxide and sodium hydroxide.

Suitable reaction temperatures are within the range of about $-10°$ to 80° C., with a range of about 0° to 25° C. being preferred. The product may be isolated by dilution of the reaction mixture with water, mild acidification and filtration.

The sulfonamides of Formula IV can be prepared by the four step reaction sequence shown in Equation 6.

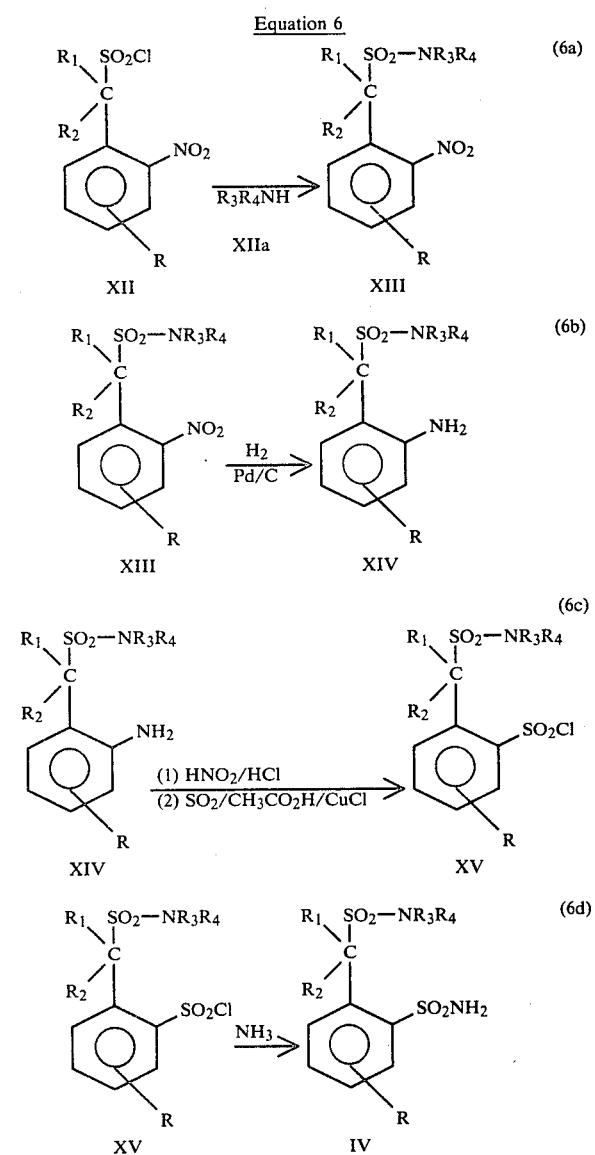

wherein R, $R_1$, $R_2$, $R_3$ and $R_4$ are as defined in Equations 1–5, with the exception that R cannot be $NO_2$.

In step 6a, the o-nitrobenzylsulfonyl chlorides of Formula XII, which are well-known in the art, are treated with an amine of Formula XIIa in an inert organic solvent such as methylene chloride, ethyl ether or tetrahydrofuran at 0°–50°. The amine may be taken in excess to act as an acid acceptor; or, alternatively, a tertiary amine such as triethylamine or pyridine may be used as an acid acceptor. The by-product amine hydrochloride is filtered off or washed out of the solvent with water and the product isolated by evaporation of the solvent.

The reduction described in step 6b is accomplished by treating a solution of the compounds of Formula XIII in a solvent such as ethanol, ethyl acetate, or diglyme, in a pressure vessel, with 50–1000 pounds per square inch of hydrogen at 25°–150° in the presence of a hydrogenation catalyst such as 5–10% palladium absorbed on carbon. When the theoretical amount of hydrogen has been absorbed, the solution is cooled and the catalyst is removed by filtration. The product is then isolated by evaporation of the solvent.

In the case where $R=NO_2$, the reduction of step 6b an be accomplished using ammonium sulfide or sodium hydrosulfide instead of catalytic hydrogenation. This type of procedure is described in *Organic Synthesis* Coll. Vol. III, pgs. 242–3, John Wiley and Sons, Inc., New York and London (1955), the disclosure of which is herein incorporated by reference.

The diazotization and coupling with sulfur dioxide, described in step 6c, is accomplished in the following manner. A solution of the aniline of Formula XIV in a mixture of concentrated hydrochloric acid and glacial acetic acid is treated with a solution of sodium nitrite in water at $-5°$ to 0°. After stirring for 10–15 minutes at 0° to insure complete diazotization, this solution is added to a mixture of an excess of sulfur dioxide, and a catalytic amount of cuprous chloride in glacial acetic acid at 0°–5°. The temperature is kept at 0°–5° for ¼ to 1 hour then raised to 20°–25° and held at that temperature for 2–4 hours. This solution is then poured into a large excess of ice water. The sulfonyl chloride products, XV, can be isolated by filtration or by extraction into a solvent such as ethyl ether or methylene chloride followed by evaporation of the solvent.

The amination described in step 6d is conveniently carried out by treating a solution of the sulfonyl chloride of Formula XV with an excess of anhydrous ammonis in a solvent such as ethyl ether or methylene chloride at 0°–25°. If the product sulfonamide, IV, is insoluble it may be isolated by filtration followed by washing out the salts with water. If the product sulfonamide is soluble in the reaction solution, it may be isolated by filtering off the precipitated ammonium chloride and evaporation of the solvent.

Compounds of Formula I, in which $W=O$ and $R_8=H$, can also be prepared by the reaction of an appropriately substituted sulfonamide, IV, with the methyl carbamate of the appropriate aminoheterocycle, XVI, in the presence of an equivalent of trimethylaluminum as shown in Equation 7.

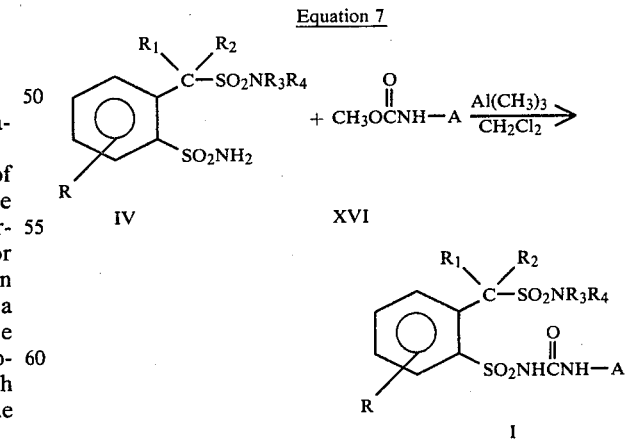

wherein R, $R_1$, $R_2$, $R_3$, $R_4$ and A are as previously defined.

The reaction of Equation 7 is best carried out in an inert solvent such as methylene chloride at 10°–45° and ambient pressure. The preferred mode of addition is to add the trimethylaluminum to a solution or slurry of the sulfonamide, IV, a mildly exothermic reaction occurs accompanied by the evolution of gas. The addition of the heterocyclic carbamate, XVI, is then made and the mixture is stirred at ambient to reflux temperatures for 6 to 48 hours. The addition of aqueous acid such as dilute hydrochloric or acetic acid removes inorganic salts from the product contained in the organic phase. Evaporation of the methylene chloride yields the crude product which can be purified by recrystallization or column chromatography.

As shown in Equation 8, compounds of Formula I, in which W is sulfur and R, $R_1$, $R_2$, $R_3$, $R_4$ and A are as previously defined and $R_8$ is H are prepared by reaction of an appropriately substituted sulfonamide, IV, with a heterocyclic isothiocyanate of Formula XVII.

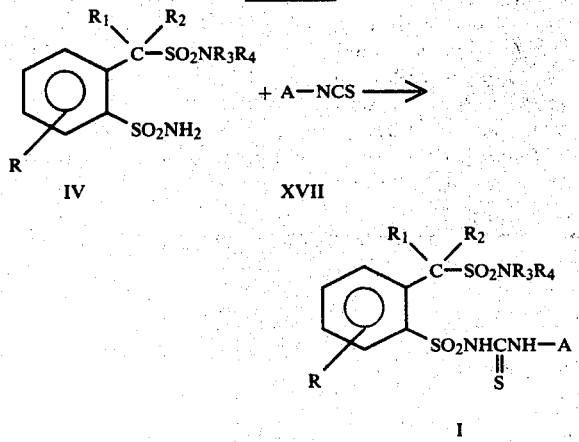

Equation 8

The reaction of Equation 8 is best carried out by dissolving or suspending the sulfonamide and isothiocyanate in a polar solvent such as acetone, acetonitrile, ethyl acetate or methyl ethyl ketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 8 are prepared, for example, according to the method of Japan Patent Application Pub: Kokai 51-143686, June 5, 1976, or that of W. Abraham and G. Barnikow, Tetrahedron 29, 691-7 (1973).

Agriculturally suitable salts of compounds of Formula I are also useful herbicides and can be prepared in a number of ways known to the art. For example, metal salts can be made by treating compounds of Formula 1 with a solution of an alkali or alkaline earth metal salt having a sufficiently basic anion (e.g. hydroxide, alkoxide, carbonate or hydride) quaternary amine salts can be made by similar techniques. Detailed examples of such techniques are given in U.S. Pat. No. 4,127,405, the disclosure of which is herein incorporated by reference.

The compounds of this invention and their preparation are further illustrated by the following examples wherein temperatures are given in degrees centigrade and all parts are by weight unless otherwise indicated.

EXAMPLE 1

2-Nitrophenylmethyl carbamimidothioate hydrochloride

A solution of 34.3 g of o-nitrobenzyl chloride and 15.2 g of thiourea in 250 ml of #2B alcohol was refluxed for 1½ hours. The solution was cooled to 60° and 250 ml of 1-chlorobutane added. Further cooling to 20° yielded a precipitate which was filtered, washed with 1-chlorobutane and dried at 65° to give 38.1 g of 2-nitrophenylmethyl carbamimidothioate hydrochloride, m.p. 190°–192°.

NMR (DMSO-$d_6$)δ: 4.85 (s, 1.8H, $CH_2$); 7.4–8 (m, 4.2H, 4 aromatics); 9.7 (broad s, 4.0H, 4 NH's).

EXAMPLE 2

N,N-Dimethyl-2-nitrobenzenemethanesulfonamide

To a slurry of 34.7 g of the compound of Example 1 in 350 ml of water was added 20.5 ml of liquid chlorine at 10°–15° over a 45 minute period. After stirring an additional 15 minutes at 10°, the precipitated sulfonyl chloride was filtered off and washed well with water. The wet sulfonyl chloride filter cake was suspended in 200 ml of ether and contacted with 18.0 ml of liquid dimethylamine at 5°–15°. After stirring at room temperature for 1½ hours, the precipitate was filtered off and washed well with water, then 1-chlorobutane. Oven drying at 60° overnight gave 15.9 g of N,N-dimethyl-2-ntrobenzenemethanesulfonamide, m.p. 129°–132°.

NMR (DMSO-$d_6$)δ: 2.7 (s, 6.2H, $SO_2NMe_2$); 4.8 (s, 1.9H, —$CH_2$—); 7.6–8.3 (m, 3.9H, 4 aromatics).

Anal. Calcd. for $C_9H_{12}N_2O_4S$: C, 44.28; H, 4.96; N, 11.47; S, 13.13. Found: C, 44.6; 44.5; H, 4.8; N, 11.4; S, 13.3. 4.7; N, 11.4; S, 13.0.

EXAMPLE 3

N,N-Dimethyl-2-aminobenzenemethanesulfonamide

In a pressure bottle, a mixture of 116 g of the product of Example 2, 1400 ml of 2-methoxyethyl ether and 10 g of 10% palladium on carbon was shaken at 110° under 500 p.s.i. hydrogen until the hydrogen was no longer absorbed. The catalyst was filtered off and the filtrate stripped under reduced pressure to a volume of 200 ml. This residue was poured into 600 ml of ice and the precipitate filtered off and dried to give 84 g of crude product, m.p. 70°–78°. Recrystallization from ∼600 ml of 1-chlorobutane gave 60.6 g of N,N-dimethyl-2-aminobenzenemethanesulfonamide, m.p. 92°–100°.

NMR (DMSO-$d_6$)δ: 2.7 (s, 5.8H, $SO_2NMe_2$); 4.3 (s, 2.1H, $CH_2$); 4.9–5.2 (broad s, 2.0H, $NH_2$); 6.4–7.3 (m, 4.1H, 4 aromatics).

EXAMPLE 4

2-[(Dimethylamino)sulfonylmethyl]benzenesulfonamide

To a solution of 53.5 g of the product of Example 3 in a mixture of 225 ml of concentrated hydrochloric acid and 75 ml of glacial acetic acid was added a solution of 21.4 g of sodium nitrite in 70 ml of water at −5° to 0°. The solution was stirred at 0° for 15 minutes, then poured into a mixture of 6 g of cuprous chloride, 48 ml of liquid sulfur dioxide in 300 ml of glacial acetic acid at 0°–4°. This mixture was stirred at 0° for 1 hour, then at 25° for 2 hours before being poured into 2 liters of ice-water. The precipitate was filtered and washed with water then suspended in 250 ml of ether and treated with 11.0 ml of liquid anhydrous ammonia at 5°–15°. After stirring at 25° for 30 minutes the precipitate was filtered off and washed well with ether then water. Oven drying at 60° gave 40.2 g of 2-[(dimethylamino)-sulfonylmethyl]benzenesulfonamide, m.p. 145°–150°.

NMR (DMSO-$d_6$)$\delta$: 2.7 (s, 6.0 H, $SO_2NMe_2$); 4.8 (s, 1.8H, —$CH_2$—); 7.2–8.1 (m, 6.2H, 4 aromatics+—$SO_2NH_2$).

EXAMPLE 5

2-[(Dimethylamino)sulfonylmethyl]benzenesulfonyl isocyanate

A solution of 14.0 g of the product of Example 4, 5.0 g of n-butyl isocyanate and 0.1 g of DABCO in 90 ml of mixed xylenes was heated to 136°. To this solution was added 3.6 ml of liquid phosgene over a 2 hour period to maintain the temperature between 125° and 136°. The temperature was kept at 130° for ½ hour after the addition. The solution was cooled, and filtered under a nitrogen atmosphere and concentrated at 60°–70° in vacuo to give 16.0 g of crude 2-[(dimethylamino)sulfonylmethyl]benzenesulfonyl isocyanate as a moisture sensitive oil. An infrared peak at 2200 cm$^{-1}$ confirmed the presence of the —$SO_2NCO$ group.

EXAMPLE 6

2-[(Dimethylamino)sulfonylmethyl]-N-[(4,6-dimethoxypyrimidin-2-yl)aminocarbonyl]benzenesulfonamide A mixture of 2.6 g of the product of Example 5, 0.9 g of 2-amino-4,6-dimethoxypyrimidine and a few crystals of DABCO in 15 ml of dry acetonitrile was heated at 50°–55° for 1 hour under a nitrogen atmosphere, then stirred overnight at room temperature. The precipitate was filtered off, washed with acetonitrile and dried to give 2.1 g of 2-[(dimethylamino)sulfonylmethyl]-N-[(4,6-dimethoxypyrimidin-2-yl)aminocarbonyl]benzenesulfonamide, m.p. 172°–176°.

NMR (DMSO-$d_6$)$\delta$: 2.8 (s, 6.3H, $SO_2NMe_2$); 4.0 (s, 5.6H, Het—$OCH_3$'s); 5.0 (s, 2.0H, —$CH_2$—); 6.1 (s, 0.8H, Het—H); 7.7–8.6 (m, 4.4H, 4 aromatics); 10.8 and 13.2 (broad singlets, NH's).

Anal. Calcd. for $C_{16}H_{21}N_5O_7S_2$: C, 41.80; H, 4.61; N, 15.24; S, 13.96. Found: C, 41.8; 42.2 H, 4.6; N, 16.1; S, 14.0. 4.5; N, 16.1; S, 14.3.

Using the procedures and examples described above and choosing the appropriate aminoheterocycle and sulfonyl isocyanate or sulfonamide, the compounds described in Tables I–VI may be prepared.

TABLE I

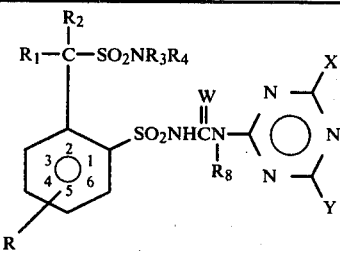

| R | $R_1$ | $R_2$ | $R_4$ | W | $R_3$ | $R_8$ | X | Y | m.p. (°C.) |
|---|---|---|---|---|---|---|---|---|---|
| H | H | H | $CH_3$— | O | $CH_3$ | H | $CH_3O$ | $CH_3O$ | 200–203° (d) |
| H | H | H | $CH_3$— | O | $CH_3$ | H | $CH_3O$ | $CH_3$ | 200–205° (d) |
| H | H | H | $CH_3$— | O | $CH_3$ | H | $CH_3$ | $CH_3$ | 209–210° (d) |
| H | H | H | $CH_3$— | O | $CH_3O$ | H | $CH_3O$ | $CH_3O$ | |
| H | H | H | $CH_3$— | O | $CH_3CH_2$— | H | $CH_3O$ | $CH_3O$ | |
| H | H | H | $CH_3$— | O | $CH_3CH_2CH_2$— | H | $CH_3O$ | $CH_3O$ | |
| H | H | H | $CH_3$— | O | $(CH_3)_2CH$— | H | $CH_3O$ | $CH_3O$ | |
| H | H | H | $CH_3$— | O | $CH_3(CH_2)_3$— | H | $CH_3O$ | $CH_3O$ | |
| H | H | H | $CH_3CH_2$— | O | $CH_3CH_2$— | H | $CH_3O$ | $CH_3O$ | |
| H | H | H | $CH_3$— | O | $CH_3$ | H | $CH_3O$ | $CH_3O$ | |
| H | H | $CH_3$ | $CH_3$— | O | $CH_3$ | H | $CH_3O$ | $CH_3O$ | |
| H | $CH_3$ | $CH_3$ | $CH_3$— | O | $CH_3$ | H | $CH_3O$ | $CH_3O$ | |
| H | H | H | $CH_3$— | O | $CH_3$ | H | $CH_3O$ | $CH_3O$ | |
| 5-F | H | H | $CH_3$— | O | $CH_3$ | H | $CH_3O$ | $CH_3O$ | |
| 5-Cl | H | H | $CH_3$— | O | $CH_3$ | H | $CH_3O$ | $CH_3O$ | |
| 5-Br | H | H | $CH_3$— | O | $CH_3$ | H | $CH_3O$ | $CH_3O$ | |
| 5-$NO_2$ | H | H | $CH_3$— | O | $CH_3$ | H | $CH_3O$ | $CH_3O$ | |
| 5-$CF_3$ | H | H | $CH_3$— | O | $CH_3$ | H | $CH_3O$ | $CH_3O$ | |
| 5-$CH_3O$ | H | H | $CH_3$— | O | $CH_3$ | H | $CH_3O$ | $CH_3O$ | |
| 5-$C_2H_5O$ | H | H | $CH_3$— | O | $CH_3$ | H | $CH_3O$ | $CH_3O$ | |
| 5-▷—O— | H | H | $CH_3$— | O | $CH_3$ | H | $CH_3O$ | $CH_3O$ | |
| 5-$CH_3$ | H | H | $CH_3$— | O | $CH_3$ | H | $CH_3O$ | $CH_3O$ | |
| 5-$C_2H_5$— | H | H | $CH_3$— | O | $CH_3$ | H | $CH_3O$ | $CH_3O$ | |
| 5-▷— | H | H | $CH_3$— | O | $CH_3$ | H | $CH_3O$ | $CH_3O$ | |
| 3-Cl | H | H | $CH_3$— | O | $CH_3$ | H | $CH_3O$ | $CH_3O$ | |
| 4-Cl | H | H | $CH_3$— | O | $CH_3$ | H | $CH_3O$ | $CH_3O$ | |
| 6-Cl | H | H | $CH_3$— | O | $CH_3$ | H | $CH_3O$ | $CH_3O$ | |
| H | H | H | $CH_3$ | O | $CH_3$ | H | Cl | $CH_3O$ | |

TABLE I-continued

| R | R₁ | R₂ | R₄ | W | R₃ | R₈ | X | Y | m.p. (°C.) |
|---|----|----|----|---|----|----|---|---|------------|
| H | H | H | CH₃ | O | CH₃ | H | Br | CH₃O | |
| H | H | H | CH₃ | O | CH₃ | H | CH₃CH₂— | CH₃O | |
| H | H | H | CH₃ | O | CH₃ | H | CH₃CH₂O— | CH₃ | |
| H | H | H | CH₃ | O | CH₃ | H | ⟩—O— | CH₃ | |
| H | H | H | CH₃ | O | CH₃ | H | CF₃ | CH₃O | |
| H | H | H | CH₃ | O | CH₃ | H | CH₃S | CH₃O | |
| H | H | H | CH₃ | O | CH₃ | H | CH₃OCH₂— | CH₃ | |
| H | H | H | CH₃ | O | CH₃ | H | CH₃OCH₂— | CH₃O | |
| H | H | H | CH₃ | O | CH₃ | H | H | CH₃ | |
| H | H | H | CH₃ | O | CH₃ | H | H | CH₃O | |
| H | H | H | CH₃ | S | CH₃ | H | CH₃O | CH₃O | |
| H | C₂H₅ | H | CH₃ | O | CH₃ | H | CH₃O | CH₃O | |
| H | n-C₃H₇ | H | CH₃ | O | CH₃ | H | CH₃O | CH₃O | |
| H | n-C₄H₉ | H | CH₃ | O | CH₃ | H | CH₃O | CH₃O | |
| H | H | H | CH₃ | O | CH₃ | CH₃ | CH₃O | CH₃O | |
| H | H | H | CH₃ | O | CH₃ | CH₃ | CH₃O | CH₃ | |
| H | H | H | CH₃ | O | CH₃ | CH₃ | CH₃ | CH₃ | |
| H | H | H | CH₃ | O | CH₃ | CH₃O | CH₃O | CH₃O | |
| H | H | H | CH₃ | O | CH₃ | CH₃O | CH₃ | CH₃O | |
| H | H | H | CH₃ | O | CH₃ | CH₃O | CH₃ | CH₃ | |

TABLE II

| R | R₁ | R₂ | R₄ | W | R₃ | R₈ | X | Y | Z | m.p. (°C.) |
|---|----|----|----|---|----|----|---|---|---|------------|
| H | H | H | CH₃— | O | CH₃ | H | CH₃O | CH₃O | CH | 172–176° (d) |
| H | H | H | CH₃— | O | CH₃ | H | CH₃O | CH₃ | CH | 181–183° (d) |
| H | H | H | CH₃— | O | CH₃ | H | CH₃ | CH₃ | CH | 203–204° (d) |
| H | H | H | CH₃— | O | CH₃O | H | CH₃O | CH₃O | CH | |
| H | H | H | CH₃— | O | CH₃CH₂— | H | CH₃O | CH₃O | CH | |
| H | H | H | CH₃— | O | CH₃CH₂CH₂— | H | CH₃O | CH₃O | CH | |
| H | H | H | CH₃— | O | (CH₃)₂CH— | H | CH₃O | CH₃O | CH | |
| H | H | H | CH₃— | O | CH₃(CH₂)₃— | H | CH₃O | CH₃O | CH | |
| H | H | H | CH₃CH₂— | O | CH₃CH₂— | H | CH₃O | CH₃O | CH | |
| H | H | H | CH₃— | O | CH₃ | H | CH₃O | CH₃O | CH | |
| H | H | CH₃ | CH₃— | O | CH₃ | H | CH₃O | CH₃O | CH | |
| H | CH₃ | CH₃ | CH₃— | O | CH₃ | H | CH₃O | CH₃O | CH | |
| H | H | H | CH₃— | O | CH₃ | H | CH₃O | CH₃O | CH | |
| 5-F | H | H | CH₃— | O | CH₃ | H | CH₃O | CH₃O | CH | |
| 5-Cl | H | H | CH₃— | O | CH₃ | H | CH₃O | CH₃O | CH | |
| 5-Br | H | H | CH₃— | O | CH₃ | H | CH₃O | CH₃O | CH | |
| 5-NO₂ | H | H | CH₃— | O | CH₃ | H | CH₃O | CH₃O | CH | |
| 5-CF₃ | H | H | CH₃— | O | CH₃ | H | CH₃O | CH₃O | CH | |
| 5-CH₃O | H | H | CH₃— | O | CH₃ | H | CH₃O | CH₃O | CH | |
| 5-C₂H₅O | H | H | CH₃— | O | CH₃ | H | CH₃O | CH₃O | CH | |
| 5-⟩—O— | H | H | CH₃— | O | CH₃ | H | CH₃O | CH₃O | CH | |
| 5-CH₃ | H | H | CH₃— | O | CH₃ | H | CH₃O | CH₃O | CH | |

TABLE II-continued

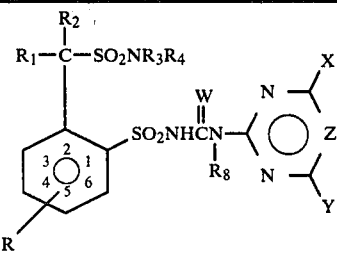

| R | R₁ | R₂ | R₄ | W | R₃ | R₈ | X | Y | Z | m.p. (°C.) |
|---|----|----|----|----|----|----|----|----|----|----|
| 5-C₂H₅— | H | H | CH₃— | O | CH₃ | H | CH₃O | CH₃O | CH | |
| 5-⟩— | H | H | CH₃— | O | CH₃ | H | CH₃O | CH₃O | CH | |
| 3-Cl | H | H | CH₃— | O | CH₃ | H | CH₃O | CH₃O | CH | |
| 4-Cl | H | H | CH₃— | O | CH₃ | H | CH₃O | CH₃O | CH | |
| 6-Cl | H | H | CH₃— | O | CH₃ | H | CH₃O | CH₃O | CH | |
| H | H | H | CH₃ | O | CH₃ | H | Cl | CH₃O | CH | |
| H | H | H | CH₃ | O | CH₃ | H | Br | CH₃O | CH | |
| H | H | H | CH₃ | O | CH₃ | H | CH₃CH₂— | CH₃O | CH | |
| H | H | H | CH₃ | O | CH₃ | H | CH₃CH₂O— | CH₃ | CH | |
| H | H | H | CH₃ | O | CH₃ | H | ⟩—O— | CH₃ | CH | |
| H | H | H | CH₃ | O | CH₃ | H | CF₃ | CH₃O | CH | |
| H | H | H | CH₃ | O | CH₃ | H | CH₃S | CH₃O | CH | |
| H | H | H | CH₃ | O | CH₃ | H | CH₃OCH₂— | CH₃ | CH | |
| H | H | H | CH₃ | O | CH₃ | H | CH₃OCH₂— | CH₃O | CH | |
| H | H | H | CH₃ | O | CH₃ | H | H | CH₃ | CH | |
| H | H | H | CH₃ | O | CH₃ | H | H | CH₃O | CH | |
| H | H | H | CH₃ | O | CH₃ | H | CH₃ | CH₃ | C—Cl | |
| H | H | H | CH₃ | O | CH₃ | H | CH₃ | CH₃ | C—CN | |
| H | H | H | CH₃ | O | CH₃ | H | CH₃ | CH₃ | C—CH₃ | |
| H | H | H | CH₃ | O | CH₃ | H | H | CH₃ | C—CH₃ | |
| H | H | H | CH₃ | O | CH₃ | H | CH₃ | CH₃ | C—CH₂CH₃ | |
| H | H | H | CH₃ | O | CH₃ | H | H | CH₃ | C—CH₂CH₃ | |
| H | H | H | CH₃ | O | CH₃ | H | Cl | Cl | C—CH₂CH₂Cl | |
| H | H | H | CH₃ | O | CH₃ | H | H | CH₃ | C—CH₂CH₂Cl | |
| H | H | H | CH₃ | O | CH₃ | H | CH₃ | CH₃ | C—CH₂CH₂Cl | |
| H | H | H | CH₃ | O | CH₃ | H | CH₃ | CH₃ | C—CH₂CH=CH₂ | |
| H | H | H | CH₃ | O | CH₃ | H | H | CH₃ | C—CH₂CH=CH₂ | |
| H | H | H | CH₃ | S | CH₃ | H | CH₃O | CH₃O | CH | |
| H | C₂H₅ | H | CH₃ | O | CH₃ | H | CH₃O | CH₃O | CH | |
| H | n-C₃H₇ | H | CH₃ | O | CH₃ | H | CH₃O | CH₃O | CH | |
| H | n-C₄H₉ | H | CH₃ | O | CH₃ | H | CH₃O | CH₃O | CH | |
| H | H | H | CH₃ | O | CH₃ | CH₃ | CH₃O | CH₃O | CH | |
| H | H | H | CH₃ | O | CH₃ | CH₃ | CH₃O | CH₃ | CH | |
| H | H | H | CH₃ | O | CH₃ | H | CH₃O | CH₃O | CH | |
| H | H | H | CH₃ | O | CH₃ | CH₃O | CH₃O | CH₃ | CH | |
| H | H | H | CH₃ | O | CH₃ | CH₃O | CH₃ | CH₃ | CH | |

TABLE III

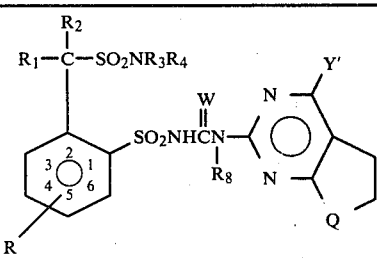

| R | R₁ | R₂ | R₄ | W | R₃ | R₈ | Y' | Q | m.p. (°C.) |
|---|----|----|----|----|----|----|----|----|----|
| H | H | H | CH₃— | O | CH₃ | H | C₂H₅O | O | |
| H | H | H | CH₃— | O | CH₃ | H | CH₃O | O | |
| H | H | H | CH₃— | O | CH₃ | H | CH₃ | O | |
| H | H | H | CH₃— | O | CH₃O | H | CH₃O | O | |
| H | H | H | CH₃— | O | CH₃CH₂— | H | CH₃O | O | |

TABLE III-continued

Structure: R₁-C(R₂)-SO₂NR₃R₄ on benzene ring (positions 1-6 numbered) with R substituent, and -SO₂NHC(=W)N(R₈)- linked to a pyrimidine ring bearing Y' and fused to a ring containing Q.

| R | R₁ | R₂ | R₄ | W | R₃ | R₈ | Y' | Q | m.p. (°C.) |
|---|----|----|-----|---|-----|-----|------|----|---|
| H | H | H | CH₃— | O | CH₃CH₂CH₂— | H | CH₃O | O | |
| H | H | H | CH₃— | O | (CH₃)₂CH— | H | CH₃O | O | |
| H | H | H | CH₃— | O | CH₃(CH₂)₃— | H | CH₃O | O | |
| H | H | H | CH₃CH₂— | O | CH₃CH₂— | H | CH₃O | O | |
| H | H | H | CH₃— | O | CH₃— | H | CH₃O | O | |
| H | H | CH₃ | CH₃— | O | CH₃— | H | CH₃O | O | |
| H | CH₃ | CH₃ | CH₃— | O | CH₃— | H | CH₃O | O | |
| H | H | H | CH₃— | O | CH₃— | H | CH₃O | O | |
| 5-F | H | H | CH₃— | O | CH₃— | H | CH₃O | O | |
| 5-Cl | H | H | CH₃— | O | CH₃— | H | CH₃O | O | |
| 5-Br | H | H | CH₃— | O | CH₃— | H | CH₃O | O | |
| 5-NO₂ | H | H | CH₃— | O | CH₃— | H | CH₃O | O | |
| 5-CF₃ | H | H | CH₃— | O | CH₃— | H | CH₃O | O | |
| 5-CH₃O | H | H | CH₃— | O | CH₃— | H | CH₃O | O | |
| 5-C₂H₅O | H | H | CH₃— | O | CH₃— | H | CH₃O | O | |
| 5-▷-O— | H | H | CH₃— | O | CH₃— | H | CH₃O | O | |
| 5-CH₃ | H | H | CH₃— | O | CH₃— | H | CH₃O | O | |
| 5-C₂H₅— | H | H | CH₃— | O | CH₃— | H | CH₃O | O | |
| 5-▷ | H | H | CH₃— | O | CH₃— | H | CH₃O | O | |
| 3-Cl | H | H | CH₃— | O | CH₃— | H | CH₃O | O | |
| 4-Cl | H | H | CH₃— | O | CH₃— | H | CH₃O | O | |
| 5-Cl | H | H | CH₃— | O | CH₃— | H | CH₃O | O | |
| H | H | H | CH₃ | S | CH₃— | H | CH₃O | O | |
| H | H | H | CH₃ | O | CH₃ | H | H | O | |
| H | H | H | CH₃ | O | CH₃CH₂ | H | CH₃ | O | |
| H | H | H | CH₃ | O | CH₃ | H | H | CH₂ | |
| H | H | H | CH₃ | O | CH₃ | H | C₂H₅O | CH₂ | |
| H | H | H | CH₃ | O | CH₃ | H | CH₃ | CH₂ | |
| H | H | H | CH₃ | O | CH₃ | H | CH₃O | CH₂ | |
| H | H | H | CH₃ | O | CH₃CH₂ | H | CH₃O | CH₂ | |
| H | C₂H₅ | H | CH₃ | O | CH₃ | H | CH₃O | O | |
| H | n-C₃H₇ | H | CH₃ | O | CH₃ | H | CH₃O | O | |
| H | n-C₄H₉ | H | CH₃ | O | CH₃ | H | CH₃O | O | |
| H | CH₃ | H | CH₃ | O | CH₃ | CH₃ | CH₃O | O | |
| H | H | H | CH₃ | O | CH₃ | CH₃ | CH₃ | O | |
| H | H | H | CH₃ | O | CH₃ | CH₃ | C₂H₅O | O | |
| H | H | H | CH₃ | O | CH₃ | CH₃O | CH₃O | CH₂ | |
| H | H | H | CH₃ | O | CH₃ | CH₃O | CH₃ | CH₂ | |
| H | H | H | CH₃ | O | CH₃ | CH₃O | C₂H₅O | CH₂ | |

TABLE IV

| R | R₁ | R₂ | R₃ | R₄ | W | R₈ | Y' |
|---|----|----|-----|-----|---|-----|-----|
| H | H | H | CH₃ | CH₃ | O | H | CH₃ |
| H | H | H | CH₃O | CH₃ | O | H | CH₃ |
| H | H | H | C₂H₅ | CH₃ | O | H | CH₃ |
| H | H | H | n-C₄H₉ | CH₃ | O | H | CH₃ |
| H | H | H | CH₃ | CH₃ | O | H | CH₃O |
| H | H | H | CH₃ | CH₃ | O | H | C₂H₅O |
| H | H | H | CH₃ | CH₃ | O | H | H |
| H | H | H | CH₃ | CH₃ | S | H | CH₃O |
| H | CH₃ | CH₃ | CH₃ | CH₃ | O | H | CH₃O |
| H | CH₃ | H | CH₃ | CH₃ | O | H | CH₃O |

TABLE IV-continued $$\text{R}\underset{5\ 6}{\overset{4\ 3}{\underset{1}{\bigcirc}}}\underset{SO_2NH-\overset{W}{\overset{\|}{C}}-N(R_8)-}{\overset{R_1\ R_2}{\overset{|\ |}{C}-SO_2NR_3R_4}}\text{(pyridinyl-Y')}$$

| R | $R_1$ | $R_2$ | $R_3$ | $R_4$ | W | $R_8$ | Y' |
|---|---|---|---|---|---|---|---|
| H | n-$C_4H_9$ | H | $CH_3$ | $CH_3$ | O | H | $CH_3O$ |
| H | H | H | $CH_3$ | $CH_3$ | O | H | $CH_3O$ |
| 3-Cl | H | H | $CH_3$ | $CH_3$ | O | H | $CH_3O$ |
| 4-Cl | H | H | $CH_3$ | $CH_3$ | O | H | $CH_3O$ |
| 5-Cl | H | H | $CH_3$ | $CH_3$ | O | H | $CH_3O$ |
| 6-Cl | H | H | $CH_3$ | $CH_3$ | O | H | $CH_3O$ |
| H | H | H | $CH_3$ | $CH_3$ | O | $CH_3$ | $CH_3$ |
| H | H | H | $CH_3$ | $CH_3$ | O | $CH_3$ | $CH_3O$ |
| H | H | H | $CH_3$ | $CH_3$ | O | $CH_3O$ | $CH_3$ |
| H | H | H | $CH_3$ | $CH_3$ | O | $CH_3O$ | $CH_3O$ |

TABLE V $$\text{R}\underset{5\ 6}{\overset{4\ 3}{\underset{1}{\bigcirc}}}\underset{SO_2NH-\overset{O}{\overset{\|}{C}}-NH-\text{(triazinyl)}}{\overset{R_1\ R_2}{\overset{|\ |}{C}-SO_2NR_3R_4}}$$

| R | $R_1$ | $R_2$ | $R_3$ | $R_4$ | Z |
|---|---|---|---|---|---|
| H | H | H | $CH_3$ | $CH_3$ | CH |
| H | H | H | $CH_3O$ | $CH_3$ | CH |
| H | H | H | $C_2H_5$ | $CH_3$ | CH |
| H | H | H | n-$C_4H_9$ | $CH_3$ | CH |
| H | H | H | i-$C_3H_7$ | $CH_3$ | CH |
| H | H | H | $C_2H_5$ | $C_2H_5$ | CH |
| H | $CH_3$ | H | $CH_3$ | $CH_3$ | CH |
| H | $C_2H_5$ | H | $CH_3$ | $CH_3$ | CH |
| H | n-$C_4H_9$ | H | $CH_3$ | $CH_3$ | CH |
| H | $CH_3$ | $CH_3$ | $CH_3$ | $CH_3$ | CH |
| 3-Cl | H | H | $CH_3$ | $CH_3$ | CH |
| 4-Cl | H | H | $CH_3$ | $CH_3$ | CH |
| 5-Cl | H | H | $CH_3$ | $CH_3$ | CH |
| 6-Cl | H | H | $CH_3$ | $CH_3$ | CH |
| H | H | H | $CH_3$ | $CH_3$ | N |
| H | H | H | $CH_3O$ | $CH_3$ | N |
| H | H | H | $C_2H_5$ | $CH_3$ | N |
| H | H | H | n-$C_4H_9$ | $CH_3$ | N |
| H | H | H | i-$C_3H_7$ | $CH_3$ | N |
| H | H | H | $C_2H_5$ | $C_2H_5$ | N |
| H | $CH_3$ | H | $CH_3$ | $CH_3$ | N |
| H | $C_2H_5$ | H | $CH_3$ | $CH_3$ | N |
| H | n-$C_4H_9$ | H | $CH_3$ | $CH_3$ | N |
| H | $CH_3$ | $CH_3$ | $CH_3$ | $CH_3$ | N |
| 3-Cl | H | H | $CH_3$ | $CH_3$ | N |
| 4-Cl | H | H | $CH_3$ | $CH_3$ | N |
| 5-Cl | H | H | $CH_3$ | $CH_3$ | N |
| 6-Cl | H | H | $CH_3$ | $CH_3$ | N |

TABLE VI $$\text{R}\underset{5\ 6}{\overset{4\ 3}{\underset{1}{\bigcirc}}}\underset{SO_2NCO}{\overset{R_1\ R_2}{\overset{|\ |}{C}-SO_2NR_3R_4}}$$

| R | $R_1$ | $R_2$ | $R_3$ | $R_4$ |
|---|---|---|---|---|
| H | H | H | $CH_3$ | $CH_3$ |
| H | H | H | $CH_3O$ | $CH_3$ |
| H | H | H | $C_2H_5$ | $CH_3$ |
| H | H | H | i-$C_3H_7$ | $CH_3$ |
| H | H | H | n-$C_4H_9$ | $CH_3$ |
| H | $CH_3$ | H | $CH_3$ | $CH_3$ |
| H | $C_2H_5$ | H | $CH_3$ | $CH_3$ |
| H | n-$C_4H_9$ | H | $CH_3$ | $CH_3$ |
| H | $CH_3$ | $CH_3$ | $CH_3$ | $CH_3$ |
| 3-Cl | H | H | $CH_3$ | $CH_3$ |
| 4-Cl | H | H | $CH_3$ | $CH_3$ |
| 5-Cl | H | H | $CH_3$ | $CH_3$ |
| 6-Cl | H | H | $CH_3$ | $CH_3$ |
| 5-F | H | H | $CH_3$ | $CH_3$ |
| 5-Br | H | H | $CH_3$ | $CH_3$ |
| 5-$NO_2$ | H | H | $CH_3$ | $CH_3$ |
| 5-$CF_3$ | H | H | $CH_3$ | $CH_3$ |
| 5-$CH_3O$ | H | H | $CH_3$ | $CH_3$ |
| 5-$CH_3$ | H | H | $CH_3$ | $CH_3$ |
| 5-i-$C_3H_7O$ | H | H | $CH_3$ | $CH_3$ |
| 5-i-$C_3H_7$ | H | H | $CH_3$ | $CH_3$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

| | Active* Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 1, line 62 and Examples 8, 12, 15, 39, 41, 52, 53, 58, 132, 138-140, 162-164, 166, 167 and 169-182.

H. Gysin and E. Knusli, U.S. Pat. No. 2,891,855, June 23, 1959, Col. 5, line 66 through Col. 5, line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Ed., Blackwell Scientific Publications, Oxford, 1968, pp. 101-103.

In the following examples all parts are by weight unless otherwise indicated.

EXAMPLE 7

| Wettable Powder | |
|---|---|
| 2-[(Dimethylamino)sulfonylmethyl]-N—[4,6-dimethyl-pyrimidin-2-yl)aminocarbonyl]benzene-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 8

| Wettable Powder | |
|---|---|
| 2-[(Dimethylamino)sulfonylmethyl]-N—[(4-methoxy-6-methylpyrimidin-2-yl)aminocarbonyl]-benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 9

| Granule | |
|---|---|
| wettable powder of Example 8 | 5% |
| attapulgite granules (U.S.S. 20-40 mesh; 0.84-0.42 mm) | 95% |

A slurry of wettable powder containing $\approx$25% solids is sprayed on the surface of attapulgite granules in a double-cone blender. The granules are dried and packaged.

EXAMPLE 10

| Extruded Pellet | |
|---|---|
| 2-[(Dimethylamino)sulfonylmethyl]-N—[(4,6-dimethoxy-pyrimidin-2-yl)aminocarbonyl]-benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, harmmed-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Oil Suspension | |
|---|---|
| 2-[(Dimethylamino)sulfonylmethyl]-N—[(4,6-dimethyl-1,3,5-triazin-2-yl)aminocarbonyl]-benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

| Wettable Powder | |
|---|---|
| 2-[(Dimethylamino)sulfonylmethyl]-N—[(4-methoxy-6-methyl-1,3,5-triazin-2-yl)aminocarbonyl]-benzenesulfonamide | 20% |
| sodium alkylnaphthalenesulfonate | 4% |
| sodium ligninsulfonate | 4% |
| low viscosity methyl cellulose | 3% |

-continued

| Wettable Powder | |
|---|---|
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

| Low Strength Granule | |
|---|---|
| 2-[(Dimethylamino)sulfonylmethyl]-N—[(4,6-dimethoxy-1,3,5-triazin-2-yl)aminocarbonyl]-benzenesulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| 2-[(Dimethylamino)sulfonylmethyl]-N—[(4,6-dimethyl-pyrimidin-2-yl)aminocarbonyl]benzene-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 15

| Solution | |
|---|---|
| 2-[(Dimethylamino)sulfonylmethyl]-N—[(4-methoxy-6-methylpyrimidin-2-yl)aminocarbonyl]-benzenesulfonamide, sodium salt | 5% |
| water | 95% |

The salt is added directly to the water with stirring to produce the solution, which may then be packaged for use.

EXAMPLE 16

| Low Strength Granule | |
|---|---|
| 2-[(Dimethylamino)sulfonylmethyl]-N—[(4,6-dimethoxy-pyrimidin-2-yl)aminocarbonyl]benzene-sulfonamide | 0.1% |
| attapulgite granules (U.S.S. 20-40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 17

| Granule | |
|---|---|
| 2-[(Dimethylamino)sulfonylmethyl]-N—[(4,6-dimethyl-1,3,5-triazin-2-yl)aminocarbonyl]benzene-sulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14-100 mesh (1410-149 microns), and packaged for use.

EXAMPLE 18

| High Strength Concentrate | |
|---|---|
| 2-[(Dimethylamino)sulfonylmethyl]-N—[(4,6-dimethoxy-1,3,5-triazin-2-yl)aminocarbonyl]benzene-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| 2-[(Dimethylamino)sulfonylmethyl]-N—[(4-methoxy-6-methyl-1,3,5-triazin-2-yl)aminocarbonyl]-benzenesulfonamide | 90% |
| dioctyl sodium sulfosuccinate | 0.1% |
| synthetic fine silica | 9.9% |

The ingredients are blended and ground in a hammer-mill to produce particules essentially all below 100 microns. The material is sifted through a U.S.S. No. 50 screen and then packaged.

EXAMPLE 20

| Wettable Powder | |
|---|---|
| 2-[(Dimethylamino)sulfonylmethyl]-N—[(4,6-dimethyl-pyrimidin-2-yl)aminocarbonyl]benzene-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Oil Suspension | |
|---|---|
| 2-[(Dimethylamino)sulfonylmethyl]-N—[(4,6-dimethoxypyrimidin-2-yl)aminocarbonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

| Dust | |
|---|---|
| 2-[(Dimethylamino)sulfonylmethyl]-N—[(4,6-dimethylpyrimidin-2-yl)aminocarbonyl]benzenesulfonamide | 10% |
| attapulgite | 10% |
| Pyrophyllite | 80% |

The active ingredient is blended with attapulgite and then passed through a hammer mill to produce particles substantially all below 200 microns. The ground concentrate is then blended with powdered pyrophyllite until homogeneous.

UTILITY

The compounds of the present invention are active herbicides. They have utility for broadspectrum pre- and/or post-emergence weed control in areas where complete control of all vegetation is desired, such as around fuel storage tanks, ammunition depots, industrial storage areas, oil well sites, drive-in theaters, around billboards, highway and railroad structures. By properly selecting rate and time of application. Some compounds of this invention may be used to modify plant growth beneficially, and also selectively control weeds in crops such as wheat and barley.

The precise amount of the compound of Formula I to be used in any given situation will vary according to the particular end result desired, the amount of foliage present, the weeds to be controlled, the crop species involved, the soil type, the formulation and mode of application, weather conditions, etc. Since so many variables play a role, it is not possible to state a rate of application suitable for all situations. Broadly speaking, the compounds of this invention are used at levels of about 0.05 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-(isopropylamino)-s-triazine (atrazine); the uracils such as 5-bromo-3-sec-butyl-6-methyluracil (bromacil); N-(phosphonomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamide); 2,4-dichlorophenoxyacetic acid (2,4-d) (and closely related compounds); 4-chloro-2-butynyl-3-chlorophenylcarbamate (barban); S-(2,3-dichloroallyl)-diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tertbutyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); $\alpha,\alpha,\alpha$-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl (methoxymethyl)acetanilide (alachlor); 1,1-dimethyl-3-($\alpha,\alpha,\alpha$-trifluoro-m-tolyl)-urea (fluometuron); and 5-[2-chloro-4-(trifluoromethyl)phenoxy]2-nitrobenzoic acid, methyl ester (acifluorfen-methyl).

The activity of these compounds was discovered in greenhouse tests. The test procedure is described and the data obtained are shown below.

TEST A

Seeds of crabgrass (Digitaria spp.), barnyardgrass (*Echinochloa crusgalli*), wild oats (*Avena fatua*), cassia (*Cassia tora*), morningglory (Ipomoea sp.), cocklebur (Xanthium spp.), sorghum, corn, soybean, rice, wheat and nutsedge tubers (*Cyperus rotundus*) were planted in a growth medium and treated pre-emergence with the chemicals dissolved in a non-phytotoxic solvent solution of the compounds of Table A. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed with a non-phytotoxic solvent solution of the compounds of Table A. Other containers of the above mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment utilizing the following rating system:

0 = no effect;
10 = maximum effect;
C = chlorosis or necrosis;
E = emergence inhibition;
G = growth retardation;
H = formative effects;
X = axillary stimulation; and
6Y = abscised buds or flowers.

The data obtained are summarized in Table A.

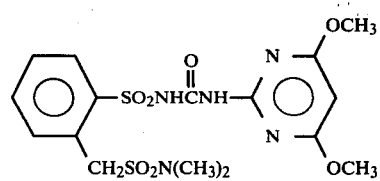

Compound 1

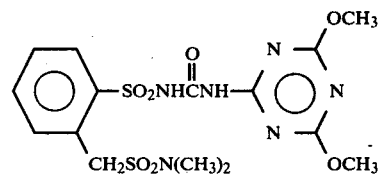

Compound 2

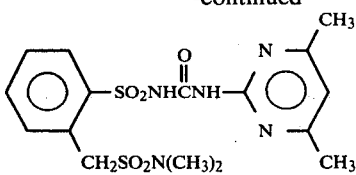

Compound 5

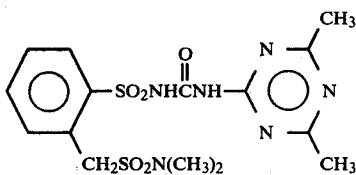

Compound 6

TABLE A

| | Compound 1 | | Compound 2 | | Compound 3 | | Compound 4 | | Compound 5 | | Compound 6 |
|---|---|---|---|---|---|---|---|---|---|---|---|
| Rate kg/ha | 0.1 | 2 | 0.1 | 2 | 0.1 | 2 | 0.1 | 2 | 0.1 | 2 | 2 |
| POST-EMERGENCE | | | | | | | | | | | |
| Bush bean | 5C,9G,6Y | 4C,9G,6Y | 1C,4G,6Y | 4S,9G,6Y | 5C,9G,6Y | 5C,9G,6Y | 2C,5G,6Y | 3C,7G,6Y | 3G | 2C,9G | 0 |
| Cotton | 5C,9G | 5C,8G | 1C | 5C,8G | 3C,3H,7G | 5C,7G | 3C,3H | 3C,4H | 1C | 2C,1H | 0 |
| Morningglory | 4C,9H | 5C,9G | 2C,5G | 3C,6G | 3C,8H | 6C,9G | 2C,4H | 3C,4G | 1C,9H | 2C | 0 |
| Cocklebur | 3C,9G | 4C,9G | 0 | 1C | 3C,9H | 4C,9G | 1C | 1C | 1C | 1C | 0 |
| Cassia | 3C,7H | 3C,6G | 1C | 1C | 3C | 3C,5G | 1C | 1C | 0 | 2G | 0 |
| Nutsedge | 1C,9G | 1C,9G | 0 | 1C,5G | 2C,6G | 3C,8G | 2G | 0 | 0 | 1C,5G | 0 |
| Crabgrass | 1C,3G | 8G | 0 | 0 | 0 | 2C,5G | 0 | 0 | 0 | 0 | 0 |
| Barnyardgrass | 3C,9H | 9C | 0 | 0 | 1C,6H | 4C,9H | 0 | 1C | 0 | 0 | 0 |
| Wild Oats | 0 | 0 | 0 | 0 | 0 | 1C,6G | 0 | 0 | 0 | 0 | 0 |
| Wheat | 0 | 0 | 0 | 0 | 0 | 3G | 0 | 0 | 0 | 0 | 0 |
| Corn | 2C,7H | 5U,9C | 0 | 0 | 2C,5H | 2C,9H | 0 | 1C,4G | 0 | 0 | 0 |
| Soybean | 3C,9G | 4C,9G | 1C,1H | 2C,4G | 2C,8G,5X | 2C,8G | 1C,3G | 1C,4G | 1C | 0 | 0 |
| Rice | 1C,5G | 8G | 0 | 2G | 1C,2G | 3C,7G | 0 | 2G | 0 | 0 | 0 |
| Sorghum | 5C,9G | 9C | 0 | 1C,2G | 3C,9H | 3C,9G | 0 | 2C,4G | 1C | 1C,3G | 0 |
| PRE-EMERGENCE | | | | | | | | | | | |
| Morningglory | 2C,5H | 9G | 0 | 3C,6G | 3C,5H | 9G | 1C | 4C,9G | 1C | 3C,8G | 0 |
| Cocklebur | 1C,3H | 9H | 0 | 6G | 9H | 9H | 0 | 2C | 0 | 9H | 0 |
| Cassia | 6C | 3C,8G | 0 | 2C | 3C,3H | 2C,8G | 2C | 2C | 0 | 2C | 0 |
| Nutsedge | 10E | 10E | 0 | 3G | 2C,6G | 10E | 1C | 8G | 0 | 5G | 4G |
| Crabgrass | 1C | 2C,8G | 0 | 0 | 2C | 2C,8G | 2G | 4G | 0 | 2C | 5G |
| Barnyardgrass | 3C,8H | 5C,9H | 0 | 1C,2G | 2C,6H | 5C,9H | 1C | 6G | 0 | 2C,6G | 1C,3G |
| Wild Oats | 1C | 3C,7G | 0 | 3G | 2C,6G | 4C,8G | 0 | 4G | 0 | 4G | 0 |
| Wheat | 1C | 4G | 0 | 4G | 2C | 1C,7G | 2G | 0 | 2G | 2G | 0 |
| Corn | 2C,9H | 9H | 0 | 3C,9H | 3C,8H | 9G | 1C,6G | 9G,2C | 1C | 2C,8H | 2C,4G |
| Soybean | 3C,5H | 9H | 0 | 2C,3G | 3C,6H | 9H | 1C | 1H,1C | 1C | 1H | 1H |
| Rice | 2C,6G | 10E | 0 | 3G | 3C,7G | 9H | 1C,4G | 2C | 2C | 5C | 1C |
| Sorghum | 2C,9G | 5C,9H | 0 | 3C,8G | 5C,8H | 4C,9H | 1C,3G | 9G,3C | 2C | 3C,7G | 2C,5G |

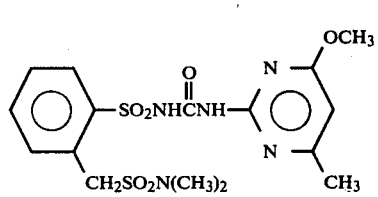

Compound 3

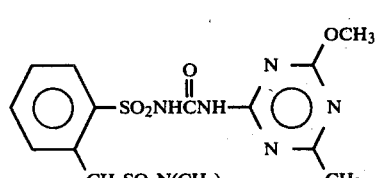

Compound 4

What is claimed is:

1. A compound of the formula:

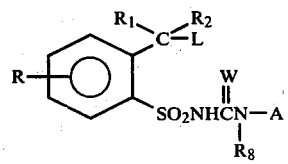

wherein
L is $SO_2NR_3R_4$;
R is H, F, Cl, Br, $NO_2$, $CF_3$, $C_1$-$C_3$ alkyl or $C_1$-$C_3$ alkoxy;
$R_1$ is H or $C_1$-$C_4$ alkyl;
$R_2$ is H or $CH_3$;
$R_3$ is $C_1$-$C_4$ alkyl or $OCH_3$;
$R_4$ is $C_1$-$C_4$ alkyl;
$R_8$ is H, $CH_3$ or $OCH_3$;

A is

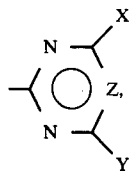

W is O or S;
X is H, Cl, Br, $CH_3$, $CH_2CH_3$, $C_1$-$C_3$ alkoxy, $CF_3$, $SCH_3$ or $CH_2OCH_3$;
Y is $CH_3$ or $OCH_3$;
Z is CH, CCl, CBr, CCN, $CCH_3$, $CCH_2CH_3$, $CCH_2CH_2Cl$ or $CCH_2CH=CH_2$;
and their agriculturally suitable salts;
provided that:
(1) when $R_3$ is $OCH_3$, then $R_4$ is $CH_3$;
(2) the total number of carbon atoms of $R_3$ and $R_4$ is five or less; and
(3) when W is S, then $R_8$ is H.

2. A compound of claim 1 wherein Z is CH, CCl, CBr or $CCH_3$, W is O, and $R_8$ is H or $CH_3$.

3. A compound of claim 2 wherein Z is CH, X is $CH_3$ or $OCH_3$, and $R_1$ and $R_2$ are H.

4. A compound of claim 3 wherein A is

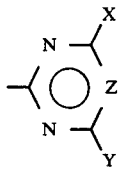

and R and $R_8$ are H.

5. A compound of claim 4 wherein $R_3$ is $C_1$-$C_3$ alkyl or $OCH_3$, and $R_4$ is $CH_3$.

6. A compound of claim 5 wherein $R_3$ is $OCH_3$ or $CH_3$.

7. The compound of claim 1, 2-[(dimethylamino)sulfonylmethyl]-N-[(4,6-dimethylpyrimidin-2-yl)aminocarbonyl]benzenesulfonamide.

8. The compound of claim 1, 2-[(dimethylamino)sulfonylmethyl]-N-[(4,6-dimethoxypyrimidin-2-yl)aminocarbonyl]benzenesulfonamide.

9. The compound of claim 1, 2-[(dimethylamino)sulfonylmethyl]-N-[(4-methoxy-6-methylpyrimidin-2-yl)aminocarbonyl]benzenesulfonamide.

10. A compound selected from:

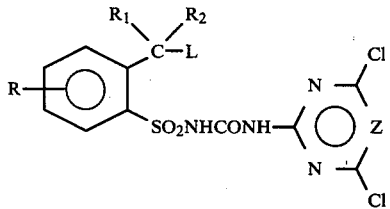

wherein
L is $SO_2NR_3R_4$;
R is H, F, Cl, Br, $NO_2$, $CF_3$, $C_1$-$C_3$ alkyl or $C_1$-$C_3$ alkoxy;
$R_1$ is H or $C_1$-$C_4$ alkyl;
$R_2$ is H or $CH_3$;
$R_3$ is $C_1$-$C_4$ alkyl or $OCH_3$;
$R_4$ is $C_1$-$C_4$ alkyl; and
Z is CH;
provided that:
(1) when $R_3$ is $OCH_3$, then $R_4$ is $CH_3$; and
(2) the total number of carbon atoms of $R_3$ and $R_4$ is five or less.

11. A composition suitable for controlling the growth of undesired vegetation which comprises an effective amount of a compound of claim 1 and at least one of the following: surfactant, solid or liquid diluent.

12. A composition suitable for controlling the growth of undesired vegetation which comprises an effective amount of a compound of claim 2 and at least one of the following: surfactant, solid or liquid diluent.

13. A composition suitable for controlling the growth of undesired vegetation which comprises an effective amount of a compound of claim 3 and at least one of the following: surfactant, solid or liquid diluent.

14. A composition suitable for controlling the growth of undesired vegetation which comprises an effective amount of a compound of claim 4 and at least one of the following: surfactant, solid or liquid diluent.

15. A composition suitable for controlling the growth of undesired vegetation which comprises an effective amount of a compound of claim 5 and at least one of the following: surfactant, solid or liquid diluent.

16. A composition suitable for controlling the growth of undesired vegetation which comprises an effective amount of a compound of claim 6 and at least one of the following: surfactant, solid or liquid diluent.

17. A method for controlling the growth of undesired vegetation which comprises applying to the locus to be protected an effective amount of a compound of claim 1.

18. A method for controlling the growth of undesired vegetation which comprises applying to the locus to be protected an effective amount of a compound of claim 2.

19. A method for controlling the growth of undesired vegetation which comprises applying to the locus to be protected an effective amount of a compound of claim 3.

20. A method for controlling the growth of undesired vegetation which comprises applying to the locus to be protected an effective amount of a compound of claim 4.

21. A method for controlling the growth of undesired vegetation which comprises applying to the locus to be protected an effective amount of a compound of claim 5.

22. A method for controlling the growth of undesired vegetation which comprises applying to the locus to be protected an effective amount of a compound of claim 6.

* * * * *